United States Patent [19]

Cawood

[11] Patent Number: 4,557,274
[45] Date of Patent: Dec. 10, 1985

[54] MIDSTREAM URINE COLLECTOR

[76] Inventor: Charles D. Cawood, 11527 N. Lou Al Ct., Houston, Tex. 77024

[21] Appl. No.: 557,668

[22] Filed: Dec. 2, 1983

Related U.S. Application Data

[63] Continuation-in-part of Ser. No. 385,927, Jun. 7, 1982, abandoned, which is a continuation-in-part of Ser. No. 310,149, Oct. 9, 1981, abandoned.

[51] Int. Cl.[4] .............................................. A47K 11/00
[52] U.S. Cl. ..................................... 128/760; 604/347; 604/349; 128/764; 128/766; 128/767
[58] Field of Search .............. 128/760, 764, 761, 763, 128/766, 767, 762; 604/347, 349, 317, 265; 4/144.1, 144.2, 144.3, 144.4

[56] References Cited

U.S. PATENT DOCUMENTS

| | | | |
|---|---|---|---|
| 3,428,046 | 2/1969 | Remer et al. | 604/265 |
| 3,499,327 | 3/1970 | Lane, Jr. | 128/760 X |
| 3,635,091 | 1/1972 | Lienger et al. | 128/761 |
| 3,716,871 | 2/1973 | Borge | 4/144.2 |
| 3,928,875 | 12/1975 | Persson | 128/767 |
| 3,929,412 | 12/1975 | Villari | 4/144.1 X |
| 4,106,490 | 8/1978 | Spilman et al. | 128/761 |
| 4,203,169 | 5/1980 | Dall | 128/767 X |
| 4,244,061 | 1/1981 | Hebskir et al. | 4/144.1 |
| 4,270,539 | 6/1981 | Michaud | 4/144.3 X |

Primary Examiner—Edward M. Coven
Attorney, Agent, or Firm—Tilton, Fallon, Lungmus

[57] ABSTRACT

A sterile midstream urine collector having an open-ended tubular body and a cup mounted therein, the cup having its open top equipped with a cover that is formed at least in part of a water-soluble material. During use of the device, the cover initially deflects a stream of urine flowing through the collector and within seconds dissolves sufficiently to allow a subsequent uncontaminated portion of the stream to enter the cup. A sample evacuation passage extends from the cup and communicates, or is adapted to communicate, with a collection tube assembly which may take the form of an air-evacuated collection tube with a piercable stopper or a syringe with a retractable plunger.

50 Claims, 17 Drawing Figures

MIDSTREAM URINE COLLECTOR

RELATED APPLICATION

This application is a continuation-in-part of my co-pending application, Ser. No. 385,927, filed June 7, 1982, abandoned which in turn was a continuation-in-part of application Ser. No. 310,149, filed Oct. 9, 1981, and now abandoned.

BACKGROUND

The importance of collecting a "midstream" sample for urine analysis is well known but, despite a widely recognized need for a simple, effective, foolproof, single-use device that a patient might use with a minimum of instruction and without assistance, no prior device meeting all such requirements has previously been known. Quite typically, the devices proposed for midstream collection have been complex in structure and operation, in some cases involving moving parts which shift from one position to another as their balance is altered by collected fluid (U.S. Pat. Nos. 3,625,064; 3,830,107; 3,635,091). In other constructions, the so-called midstream sample is collected as a result of an overflow operation (U.S. Pat. Nos. 4,040,791; 3,943,770; 4,276,889). While some prior devices avoid the shortcomings of others, the need has nevertheless remained for a relatively simple device that has no serious defects or deficiencies in design and/or operation.

SUMMARY OF THE INVENTION

An important aspect of this invention therefore lies in providing an uncomplicated low-cost midstream urine collector that requires practically no instruction for proper use and is relatively foolproof in operation. More specifically, this invention is concerned with a sterile device that automatically bypasses the contaminated initial portion of the stream, then collects a sterile or at least relatively uncontaminated midstream sample, when a user voids into the funnel-shaped top of the device. Thereafter, the collected sample is quickly and easy transferred to a sterile collection tube removably supported by the device. Because of its simplicity and low-cost construction, the device is suitable for manufacture and marketing as a disposable item for one-time use.

In all forms of the device, the midstream urine collector has an open-ended tubular body, the upper end of the body preferably having a funnel-shaped configuration. A cup member having an upwardly-directed mouth is mounted within the flow passage extending through the body. The dimensions of the cup member are substantially smaller than those of the passage to permit the downward flow of urine through the passage past the cup member and into a toilet bowl or other receptacle. Ideally, the funnel portion of the body includes a downwardly and inwardly sloping flange that helps direct urine flowing at higher velocity towards the mouth of the cup member, the flange having circumferentially-spaced recesses or notches which also allow urine flowing at lower velocity to pass directly downwardly without entering the cup member or without impinging on its cover.

In one embodiment, the cover for the cup member takes the form of an imperforate urine-deflecting membrane extending over the mouth of the cup member, the membrane being formed of a non-contaminating water-soluble polymeric material capable of disintegrating within a few seconds upon direct exposure to the stream of urine. Thus, when a patient voids into the funnel-shaped collector, an initial portion of the stream is deflected away from the cup and flows through the collector but, shortly thereafter, in an interval within about 2 to 15 seconds (preferably 3 to 8 seconds), the water-soluble cover disintegrates to allow a portion of the midstream to enter the open-topped cup member.

In a second embodiment the imperforate urine-deflecting cover is formed substantially entirely of a water-insoluble material; however, it is supported upon the cup member for movement between a first position in which it covers the mouth of, and deflects urine away from, the cup member, and a second position where it is displaced from the mouth to allow a midstream sample to enter the cup. The cover may be urged into its second position by a spring, gravity, or other suitable means. The means for normally holding the cover in its first position takes the form of a water-soluble connecting portion of the cover that is exposed directly to the flow of urine when the device is in use. Thus, the cover in its first position deflects urine away from the cup but, as soon as the water-soluble connecting portion dissolves (within 2–15 seconds, preferably 3–8 seconds) the cover shifts into its second position allowing an uncontaminated midstream sample to be collected within the cup.

The lower end of the cup member communicates with an evacuation passage that leads to a collection tube assembly. In one form of the invention, the collection tube assembly includes an air-evacuated tube having a piercable stopper that is slidably supported adjacent a hollow spike communicating with the evacuation passage. After the patient has finished voiding, the collector is simply placed upon any unyielding support surface and the evacuator collection tube is urged axially to cause piercing of the stopper and the flow of at least a portion of the midstream sample into the sterile tube. In another form of the invention, the collection tube assembly includes a syringe detachably connected to the spike of the evacuation passage and having a plunger that may be retracted prior to such detachment for the purpose of drawing at least a portion of the midstream sample from the cup member into the sterile syringe. The syringe is most advantageously provided with a self-sealing stopper through which the hollow spike extends when the collector is supplied to the user. Therefore, after the patient has finished voiding, the plunger of the syringe is retracted to transfer the urine sample from the cup and, thereafter, the syringe with its sterile midstream sample is detached from the remainder of the collector for transmission to a laboratory and analysis of its contents.

Other features, objects, and advantages of the invention will become apparent from the specification and drawings.

DETAILED DESCRIPTION

Referring to FIGS. 1–5 of the drawings, the numeral 10 generally designates a midstream sample collector comprising a tubular body 11 having an upper inlet 12, a lower outlet 13, and a flow passage 14 therebetween. The body is funnel-shaped, the lower section 11a of the body being generally cylindrical and the upper section 11b being frusto-conical in configuration. Inlet 12 is therefore substantially larger than outlet 13. The lower section 11a is provided with a plurality of outwardly projecting legs 15 so that the collector may be stood upon a tabletop or other support surface in the upstanding position depicted in FIG. 1.

Figure 1:
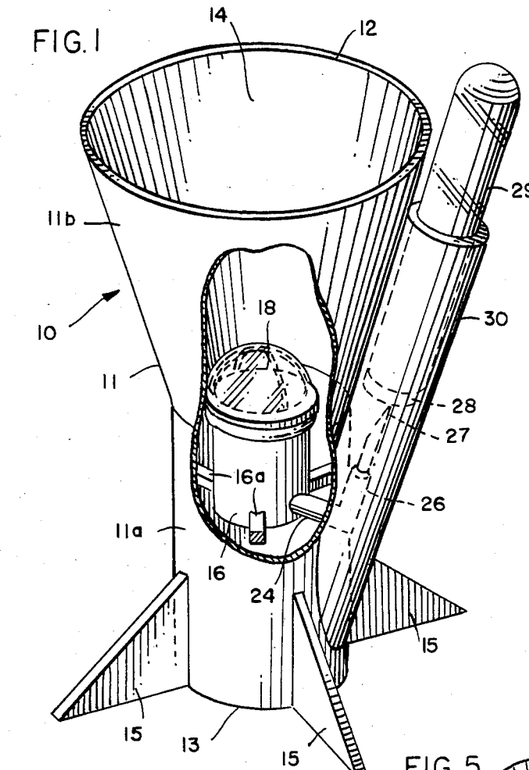
FIG. 1 is a perspective view of a midstream collector embodying the present invention.

Within the flow pasage 14 of body 11 is a cup member 16. The cup member has an upwardly-directed mouth 17, is generally coaxial with body 11, and is preferably mounted within the upper portion of the body's lower section 11a. Bridging means in the form of struts 16a support the cup member within the flow passage of the collector body. It is to be noted that the cup member is substantially smaller than the body and, in particular, has an outer diameter smaller than the inside diameter of body 11. Consequently, fluid entering the inlet of the funnel-shaped body may flow downwardly through passage 14 past cup member 16 and be discharged through outlet 13.

Figure 2:
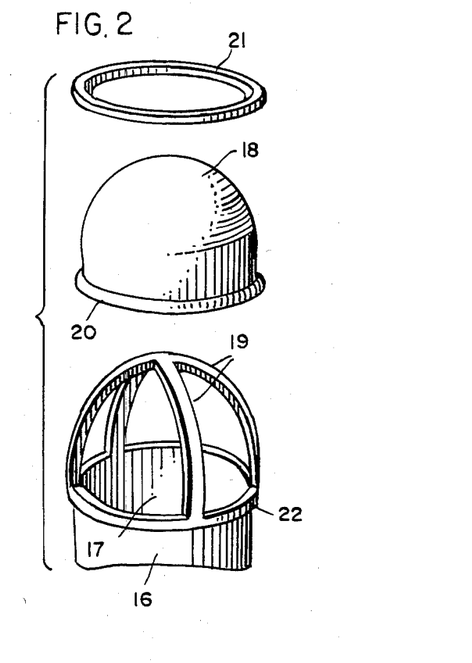
FIG. 2 is an exploded fragmentary perspective view illustrating a portion of the cup member, the covering membrane for that member, and means for attaching the cover in place.

Cover means 18 extends over the mouth 17 of cup member 16. In the embodiment shown, the cover is formed entirely, or substantially so, of water-soluble polymeric material capable of rapidly disintegrating upon direct exposure to an aqueous fluid (urine). The cover is shown to be dome-shaped; however, other configurations might be suitable such as, for sample, a conical configuration or a sloping planar configuration. In any event, it is important that the imperforate cover 18 present an upwardly-facing outer surface capable of deflecting fluid entering the flow passage of the body through inlet 12. To maintain the cover in domed condition, cup member 16 may be provided with a framework of arched supporting struts 19 (FIG. 2). The thin dome-shaped cover 18 may be provided with a circumferential beaded portion 20 about its lower periphery (which may or may not be water-soluble) so that the cover may be locked in place upon the cup member 16 by a resilient attachment ring 21 disposed about the cover, between bead 20 and an annular flange or rim 22 about the mouth of the cup member, in the manner depicted most clearly in FIG. 3.

Figure 3:
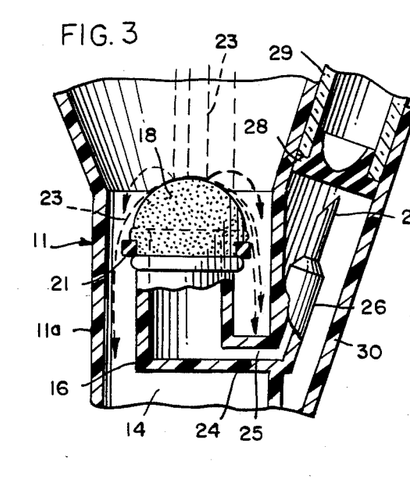
FIG. 3 is a fragmentary vertical sectional view schematically depicting the operation of the device at the beginning of a sample-collecting procedure.
Figures 4, 5:
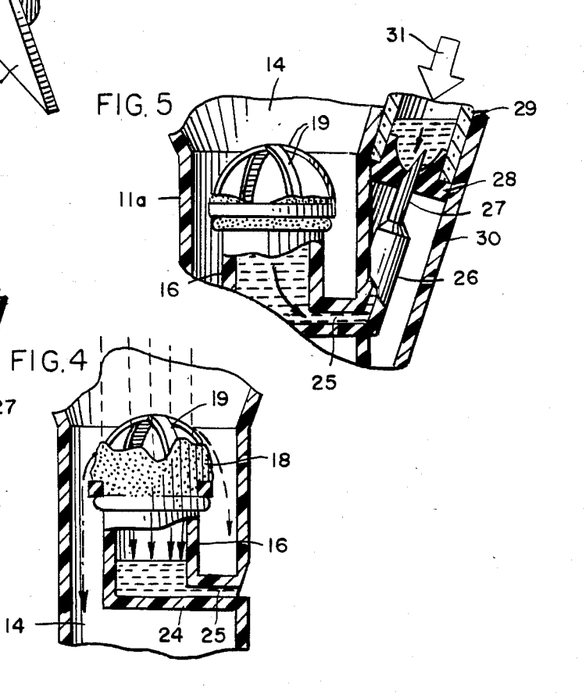
FIG. 4 is a sectional view similar to FIG. 3 but illustrating the device after the cover member has started to disintegrate and a midstream sample has begun to enter the cup member.
FIG. 5 is a sectional view similar to FIGS. 3 and 4 but illustrating the further step of transferring the midstream sample from the cup member to an evacuated collection tube.

As stated, cover 18 consists essentially of a thin membrane formed of water-soluble polymeric material, and such material should not contaminate the fluid that contacts and dissolves it. The term "non-contaminating" is used here to mean any material that when dissolved in a fluid sample will not have any significant effect on the results of tests that may subsequently be performed on that sample. A particularly effective material for such purposes has been found to be a polyvinyl alcohol film of the type marketed by Polymer Films, Inc., Rockville, Connecticut, under the designation PVOH 17-35-1; however, other water-soluble non-contaminating polymeric materials might be used such as, for example, methyl cellulose and derivatives thereof. The thickness of the film or membrane may be varied depending on the material used but, in any event, the composition and thickness of the membrane should be such that disintegration of the cover commences (i.e., one or more openings develop) within a period of about 2 to 15 seconds when the cover is directly exposed to a stream of urine. Preferably, such disintegration should commence within about 3 to 8 seconds. Consequently, when a patient voids into the sterile tubular collector, the initial contaminated portion of the stream (contaminated by the labia in the female and the foreskin and distal urethra in the male) is deflected by the cover and bypasses cup member 16. Such deflected bypassing flow is represented by arrows 23 in FIG. 3. After a few seconds, the membrane cover 18 begins to disintegrate, allowing a midstream portion of the flow to enter the cup member (FIG. 4). Complete bypassing of the cup member again occurs after that member has become completely filled with the relatively uncontaminated midstream portion of the flow of urine. Once urination is completed, the midstream portion remains collected in the cup member, with the beginning and terminal portions of the stream having been passed through the funnel-shaped body and into the toilet bowl.

Means are provided for extracting the sample from the cup member and transferring such sample to a sterile collection tube. Referring to the drawings, it will be seen that a tubular arm 24 has an evacuation passage 25 communicating with the lower end of the cup member. A tubular spike 26 projects upwardly and outwardly from the wall of the lower body section 11a and its lumen constitutes an extension of evacuation passage 25. As shown most clearly in FIGS. 1 and 3, the spike is provided with a pointed upper end 27 spaced slightly below the stopper 28 of a conventional air-evacuated collection tube 29. The collection tube may be of the same type commonly used with double-pointed needles for the collection of blood samples such as, for example, the collection tubes sold under the "Vacutainer" designation by Becton, Dickinson & Company, Rutherford, New Jersey.

The collection tube 29 is snugly but slidably supported within a tubular collar 30 that extends alongside the upper and lower sections of body 11. Normally, the tube 29 is supported above the tip of spike 27 as shown in FIG. 3. After a midstream sample has been collected within cup member 16, the collection tube 29 is urged axially downwardly in the direction represented by arrow 31 in FIG. 5 to cause the tip 27 of spike 26 to pierce the membrane of stopper 28. Since the tube 29 is supplied in evacuated condition, the piercing of the membrane causes liquid to flow from cup member 16 into the collection tube (FIG. 5). The stopper 28 is self-sealing, again as well known in the art; hence, upon removal of the collection tube from the device 10, stopper 28 automatically shields and protects the collected sample against contamination.

Tube 29, being a conventional collection tube used in clinical chemical analysis, may function as a centrifuge tube. Therefore, the collected urine specimen is disposed in a container suitable for processing by the laboratory. The urine specimen, being collected in a sealed laboratory tube without manipulations that might expose that sample to contamination (such as might occur in manually transferring a sample from one container to another for laboratory analysis), should be in a condition that diminishes the possibility of false-positive or false-negative laboratory determinations.

It is believed apparent that the device disclosed herein is relatively easy for a patient to use with a minimum of instruction and with little or no assistance by a nurse or doctor. Unlike conventional techniques, in which a patient must commence urinating, then introduce a collection container into the mid-portion of the stream, and then withdraw the container before urination has stopped, the procedure for using the device of this invention allows the collector to be positioned prior to voiding and to remain in that position until voiding is completed. The device automatically extracts the relatively uncontaminated midstream portion, allowing the initial and terminal portions of the stream to pass through the device and into the toilet. Following urination, the collector 10 is simply placed upon a stable support surface, and the patient, nurse, or other person urges the air-evacuated collection tube 29 axially downwardly to cause the collected sample to be transferred from the cup member to that tube.

The collector has been described herein as involving two stages of operation, namely, a first stage of collecting the midstream sample in the cup, and a second stage of piercing the stopper membrane and evacuating the fluid from the cup into the collection tube. Alternatively, the piercing step might conceivably be undertaken in advance of voiding, so that urine is transferred to the collection tube by pressure differential as soon as the dome-like cover begins to disintegrate and the urine enters the cup. While such a procedure may have some advantages, such as the utilization of negative pressure within the cup to accelerate or at least promote disintegration of the cover film, such advantages are believed to be offset by problems of maintaining a vacuum condition within the cup prior to fluid-disintegration of the cover film, and insuring reliability and completeness in the transfer of urine from the cup to the collection tube.

The embodiment of FIGS. 6-9 is substantially the same in structure and operation as the embodiment of FIGS. 1-5 except for the cup 16' and the cover means 18'. Cover means 18' includes a first portion 100 of water-insoluble material that extends over the mouth 101 of the cup 16' and normally prevents fluid flowing downwardly through the funnel from entering the cup. A spring element 102 has one end secured to the disc-shaped cover portion 100 and its opposite end joined to cup 16' or otherwise immobilized with respect to cup 16'. The spring element exerts a force on the cover plate tending to pivot that plate from the first or closed position shown in solid lines in FIG. 6 to the second or open position depicted in phantom in that figure. However, the action of the spring is resisted by a second portion 103 of the cover means which is secured to both the cup and tube portion 100 and holds the plate in its closed position. Cover portion 103 is formed of a film of polyvinyl alcohol or any other non-contaminating water-soluble polymeric material capable of dissolving within a period of about 2 to 15 seconds (preferably about 3 to 8 seconds) upon direct exposure to urine flowing downwardly through tubular body 11.

Figure 6:
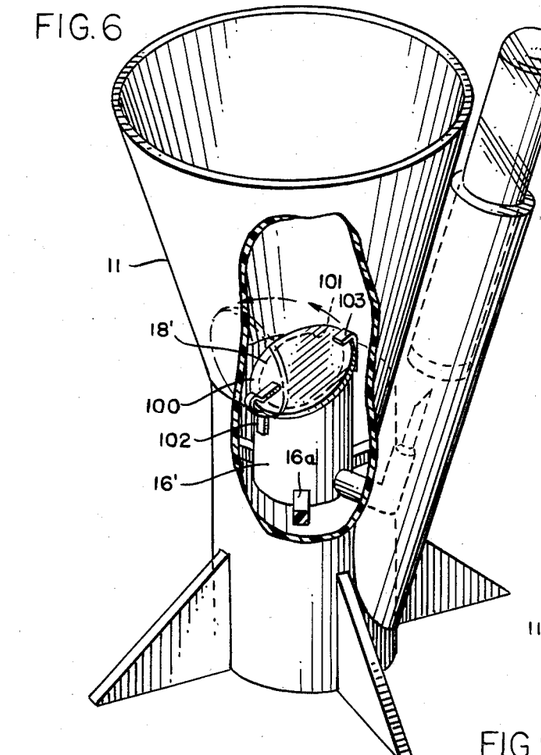
FIG. 6 is a perspective view of a midstream collector constituting a second embodiment of the invention.
Figure 7:
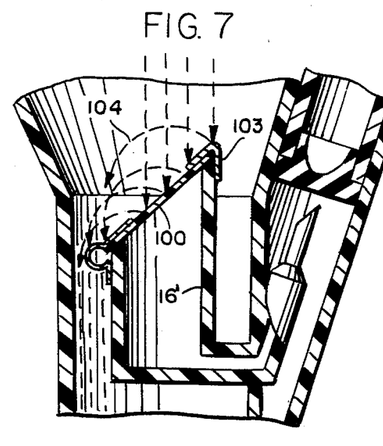
FIG. 7 is a fragmentary vertical sectional view schematically depicting the operation of the device of FIG. 6 at the beginning of a sample-collection procedure.
Figures 8, 9:
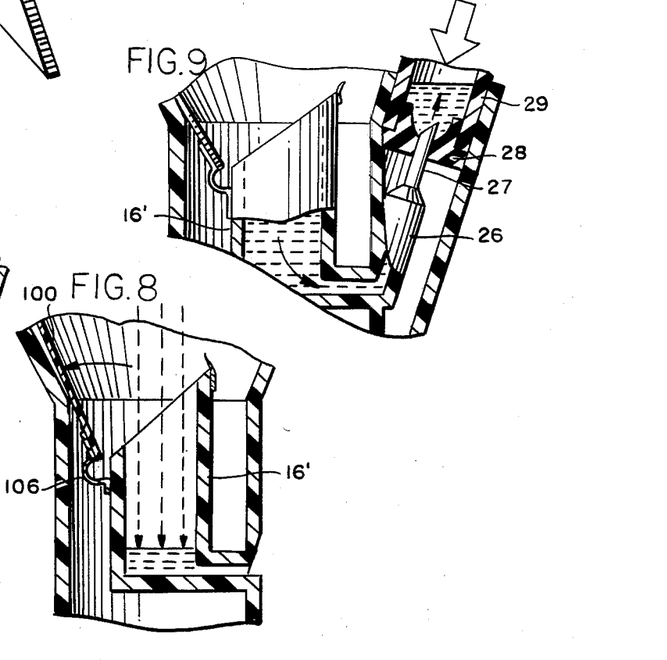
FIG. 8 is a sectional view similar to FIG. 7 but illustrating the device after the water-soluble connecting portion of the cover has disintegrated, the cover has swung into its second or open position, and a midstream sample has begun to enter the cup member.
FIG. 9 is a sectional view similar to FIGS. 7 and 8 but illustrating the further step of transferring the midstream sample from the cup member to an evacuated collection tube.

FIGS. 7-9 further illustrate the sequence of steps in the use of the collector of FIG. 6. When a patient voids into the collector, the initial contaminated portion of the stream of urine is deflected by the imperforate cover portion 100 as indicated by arrows 104 in FIG. 7. Some of the urine directly contacts the water-soluble connecting portion 103 and, after a few seconds, that portion distingrates, allowing the relatively rigid cover portion 100 to pivot into its open or second position under the influence of spring element 103 (FIG. 8). The midstream portion of the flow of urine begins to fill cup 16'. Once urination is completed, the midstream portion remains collected in the cup member, with the beginning and terminal portions of the stream having been bypassed through the funnel-shaped body into the toilet bowl. Collection tube 29 is then urged axially downwardly as previously described to cause the tip 27 of spike 26 to pierce the membrane of stopper 28. Liquid then flows from cup member 16' into the evacuated collection tube 29 as represented in FIG. 9.

It will be noted that the upper edge defining the mouth of cup member 16' extends along a sloping plane so that when the planar cover plate portion 100 is in its lowered or closed position fluid will be deflected laterally as shown in FIG. 7. The angle of incline is not critical, but it should be sufficient to promote effective bypassing of the cup assembly by the initial portion of a stream of urine flowing downwardly through the funnel.

In the embodiment of FIGS. 6-9, the water-insoluble deflecting portion 100 of the cover means 18' is shifted from its first (closed) position to its second (open) position by means of spring 102. In the additional embodiment depicted in FIG. 10, the water-insoluble deflecting portion 100' shifts from one position to the other under the influence of gravity. Specifically, the imperforate cover portion 100' is normally held in position by the connecting portion 103', thereby sealing the mouth of cup member 16". The connecting portion 103' is formed of the same material as the water-soluble non-contaminating cover portions in the previous embodiments (for example, polyvinyl alcohol), with the result that urine entering the body of the collector will initially be deflected by the sloping cover portion 18" and then, as connecting portion 103' disintegrates, cover portion 18" will slide away from the mouth of the cup 16", dropping into the lowered position depicted in broken lines in FIG. 10. The relatively uncontaminated midstream portion of the flow of urine may then enter the cup 16", and the collected sample may be transferred to an evacuated collection tube 29 in the same manner described in connection with the prior embodiments.

Figure 10:
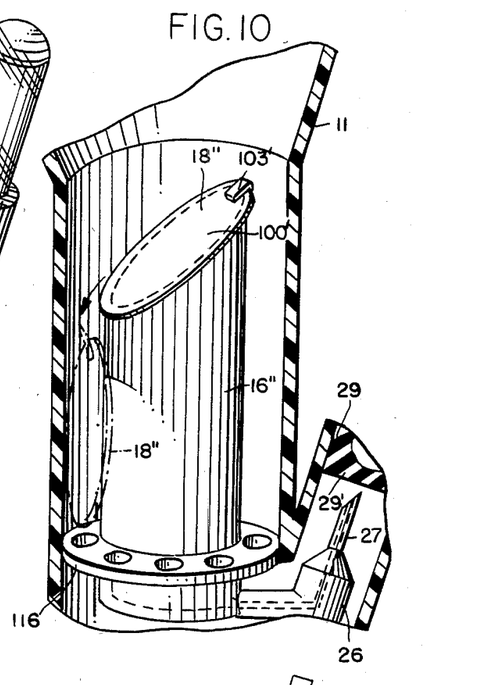
FIG. 10 is a fragmentary sectional perspective view illustrating a third embodiment of the invention.

Since gravity is primarily responsible for shifting the cover portion 18" into its second position (fluid impinging on portion 18" also exerts a lateral force tending to dislodge the cover portion), the mouth of the cup member 16" must extend along a sloping plane having a sufficient incline to cause the imperforate insoluble portion 18" to slide out of position when the connecting portion 103' is dissolved. In general, the angle of inclination should be at least 30° measured from the horizontal, with angles in the range of 45° to 60° being preferred.

Except as already noted, the physical differences between the three embodiments described above are not of major consequences. Thus, in the embodiments of FIGS. 1 and 6, the cup members 16 and 16' are supported by struts 16a and 16a", whereas, in FIG. 10 the cup member 16" is supported by an apertured annular support member 116. Such structural differences are insignificant to the extent they do not alter the operation or purpose of the components involved.

Referring to the embodiment of FIGS. 11–17, the collector 210 again has a tubular body 211 defining an upper inlet 212, lower outlets 213, and a flow passage 214 therebetween. The lower section 211a of the body is generally cylindrical and the upper section 211b is frusto-conical. It will be noted, however, that the upper section 211b includes an annular flange or skirt portion 250 that projects into the upper end of the lower section 211a and is provided with a plurality of circumferentially-spaced notches or recesses 251. In the form shown, six such notches are provided; however, a greater or smaller number may be formed in the flange of section 211b. The diameter of the opening 252 defined by that flange portion should approximate, and preferably slightly exceed, the diameter of cup member 216. As a result, the outer limits of the notches or recesses 251 are outboard of the cup member. Urine entering the funnel section at relatively low velocity tends to escape through notches 251 and travel downwardly along the path represented by dashed arrow 253 in FIG. 14, thereby entering passage 214 without impinging on the cover means 218 extending over the mouth of the cup member. On the other hand, urine flowing at greater velocity will be directed by the conical wall of section 211b into contact with the cover, as represented by solid arrows 254. Since the rate of flow during urination may be plotted along a generally bell-shaped curve, with the relatively lower rates occurring at the beginning and end, it is believed apparent that the V-shaped notches or grooves will allow the contaminated initial portion (and final portion) of the stream to bypass the membrane cover 218 while the more rapid and uncontaminated midstream portion will be directed by the flanged conical upper section of the collector into contact with the cover.

Cup member 216 and its membrane cover means 218 are similar to previously-described elements 16 and 18, respectively. Construction is simplified somewhat, with cup member 216 having a mouth 217 formed by edges 255 extending along a pair of upwardly and inwardly sloping planes (FIG. 13), but functionally the two constructions are essentially the same. The thin water-soluble polymeric cover 218 is generally dome-shaped when fitted upon the cup member (FIG. 14) and may be held in place upon that cover by a stretchable band or attachment ring 221. The composition of the cover membrane 218 and its rate of disintegration when exposed to a stream of urine are the same as described in connection with the embodiment of FIGS. 1–5.

As in previous embodiments, the embodiment of FIGS. 11–17 is provided with means for extracting the sample from the cup member and transferring that sample to a sterile collection tube. Base plate 256 has an evacuation passage 225 communicating with the lower end of the cup member and also with an upwardly-projecting tubular spike 226 disposed alongside the body of the collector. The spike may be formed of stiff but nevertheless slightly flexible polymeric material and may even be formed integrally with base plate 256. Regardless of the material selected for the spike, the spike, or the hub 226a from which it projects, should be capable of a limited extent of lateral tipping or bending action for reasons hereinafter described.

It has been found that base plate 256, cup member 216, and the lower section 211a of the collector may all be molded in one piece and that evacuation passage 225 may be molded as a channel that is open along the underside of the base plate and later closed during manufacture by a strip 257 secured to the plate's bottom surface by adhesive or by any other suitable means. For example, the strip 257 may take the form of a piece of adhesive tape sealed to the bottom of the base plate to complete the passage 225 as shown.

Unlike the collection tube assemblies 29 of the previous embodiments, assembly 229 is in the form of a syringe having an outer tube or barrel 258 and a plunger 259. The tip 260 of the syringe is equipped with a resilient stopper 261 through which spike 226 extends. The stopper may be formed of soft rubber or any other elastomeric material capable of self-sealing when the syringe and its stopper are detached from the spike.

Figures 11, 12, 13, 14:
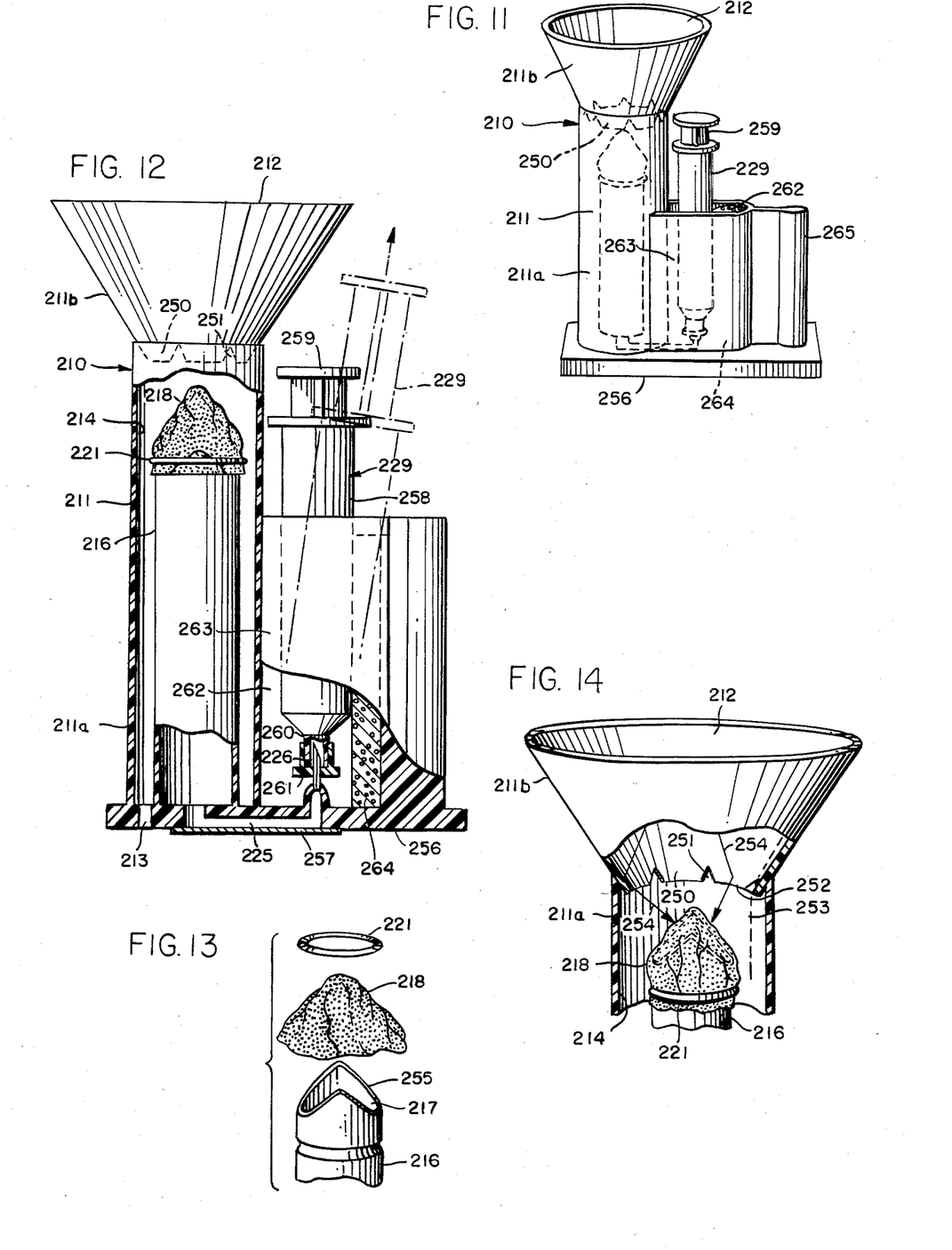
FIG. 11 is a perspective view illustrating a fourth embodiment of the invention.
FIG. 12 is a side elevational view, shown partly in section, of the embodiment of FIG. 11.
FIG. 13 is an exploded perspective view showing the cup member, covering membrane, and attaching means for the fourth embodiment.
FIG. 14 is a fragmentary perspective view, shown partly in section, illustrating the notched flange construction of the funnel and schematically depicting its action with respect to urine flowing at relatively high and relatively low velocities.
Figure 15:
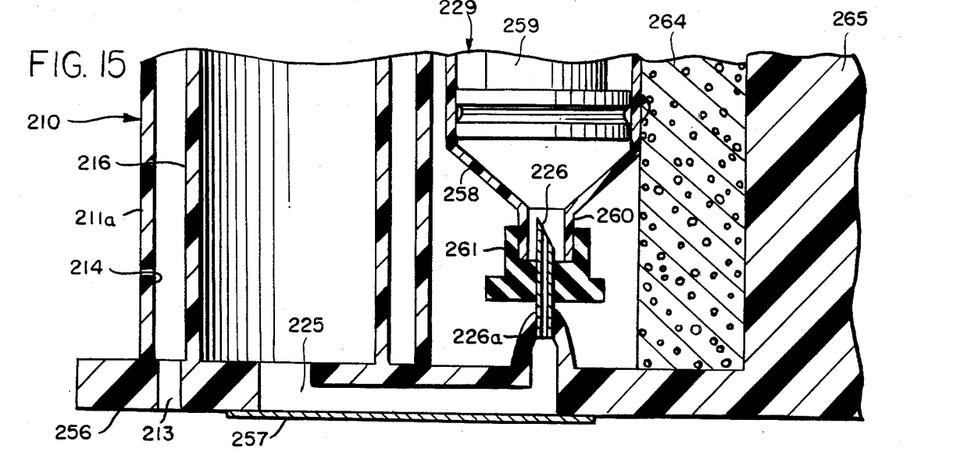
FIG. 15 is an enlarged fragmentary vertical sectional view of the lower end portion of the collector of FIG. 11.
Figure 16:
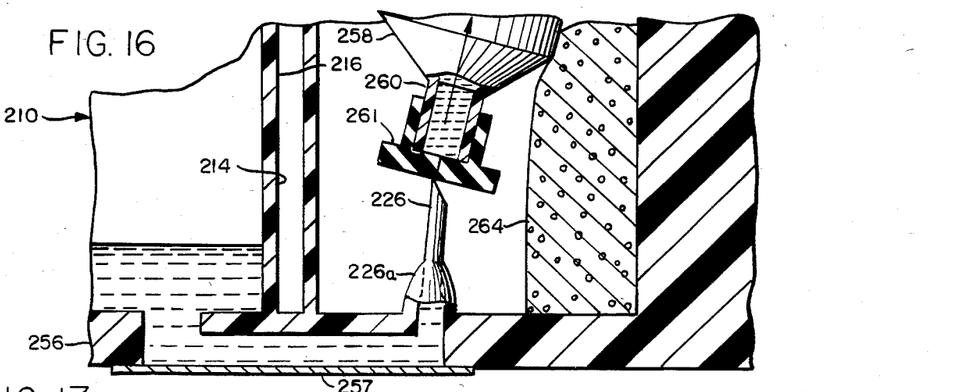
FIG. 16 is similar to FIG. 15 but shows the syringe as it is separated from the spike of the collector.
Figure 17:
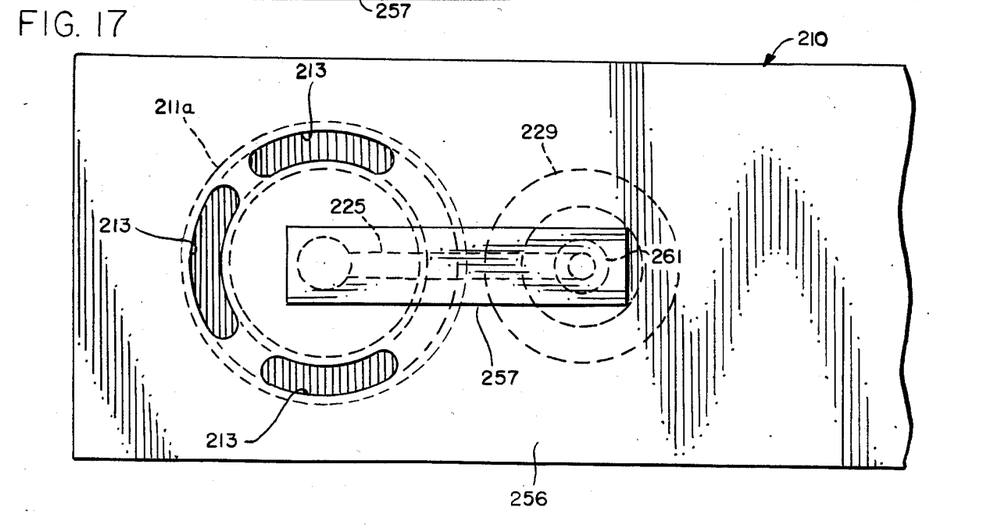
FIG. 17 is a bottom view of the collector of FIG. 14.

Referring to FIGS. 11 and 12, the syringe 229 is shown to be located within the open-topped cavity 262 of a housing 263 that may be formed integrally with base plate 256 and body section 211a. Also located within the same cavity is a resilient foam insert 264, the syringe 229 being interposed between the foam insert and body section 211a. Normally, the syringe is disposed in parallel with tubular body section 211a; however, because of the flexibility of the spike and/or its mounting and the resilience of the stopper through which it extends, the upper end of the syringe may be tipped or pivoted outwardly as indicated in broken lines in FIG. 12. The foam insert 264 helps restrain accidental outward tipping movement of the syringe and, in general, maintain the syringe beneath the umbrella of conical upper section 211b, thereby reducing exposure of the syringe and the possibility that the retracted plunger 259 might accidentally be lifted or drawn upwardly prior to sample collection.

To facilitate its manipulation and use, collector 210 may also be provided with a handle portion 265 which may be molded integrally with housing 263 and base plate 256.

The collector 210 would be supplied to the user in sterile condition in the form illustrated in FIG. 11. Following collection of a midstream sample in cup member 216, the user (or nurse or other attendant) simply places the collector upon a stable support, tips the syringe 229 outwardly, and lifts the plunger 259 to draw the midstream sample from cup member 216 into the chamber of the syringe. Thereafter, the syringe is removed from spike 226 (FIG. 16) and the urine specimen, sealed within the barrel of the syringe or collection tube because of the self-sealing properties of stopper 261, may be transported to a laboratory. There the contents may be removed for analysis by detaching stopper 261, or by inserting a suitable discharge spike through the stopper, and then urging the extended plunger downwardly.

It is believed apparent that the embodiment of FIGS. 11-17 may be provided with the air-evacuated collection tube assembly of the previous embodiments and, conversely, the previous embodiments may be equipped with a collection tube assembly in the form of the syringe of FIGS. 11-17. In each of the embodiments, the urine-deflecting cover means 18, 18', 18", and 218 has at least a portion thereof formed of a non-contaminating water-soluble polymeric material capable of disintegrating within 2 to 15 seconds upon direct exposure to a stream of urine, and in each embodiment the cover means has a first operative state wherein the water-soluble portion is intact so that the cover means closes the mouth of the cup member and deflects the initial portion of a stream of urine entering the passage and impinging on such cover means. In addition, in all embodiments the cover means has a second operative state wherein the water-soluble portion is dissolved by exposure to urine so that the mouth of the cup member is exposed to receive an uncontaminated subsequent portion of the urine stream. Finally, in all embodiments the device may be provided with an evacuation passage leading to a sample collection assembly into which the midstream sample received by the cup member is transferred.

While in the foregoing I have disclosed embodiments of the invention in considerable detail for purposes of illustration, it will be understood by those skilled in the art that many of these details may be varied without departing from the spirit and scope of the invention.

I claim:

1. A sterile midstream urine collector comprising a tubular body having an upper inlet, a lower outlet, and a flow passage therebetween; a cup member having an upwardly-directed mouth and being mounted within said passage below said inlet; said cup member being substantially smaller than said passage to permit the downward flow of urine through said passage past said cup member; and urine-deflecting cover means having at least a portion thereof formed of a non-contaminating water-soluble polymeric material capable of disintegrating within 2 to 15 seconds upon direct exposure to a stream of urine; said cover means having a first operative state wherein said portion is intact and said cover means closes the mouth of said cup member and deflects the initial portion of a stream of urine entering said passage and impinging on said cover, and a second operative state wherein said portion of said cover means is dissolved by exposure to an initial portion of a stream of urine and the mouth of said cup member is exposed to receive an uncontaminated subsequent portion of said stream.

2. The collector of claim 1 in which said water-soluble polymeric material is capable of disintegrating within 3 to 8 seconds upon exposure to a stream of urine.

3. The collector of claims 1 or 2 in which said cover means includes a water-insoluble deflecting portion normally disposed in a first position extending over the mouth of said cup member when said cover means is in said first operative state, and means urging said deflecting portion into a second position displaced from the mouth of said cup member when said cover means is in its second operative state; said water-soluble portion of said cover means normally holding said deflecting portion in its first position but allowing said deflecting portion to shift into said second position when said water-soluble portion is dissolved.

4. The collector of claim 3 in which said means for urging said deflecting portion into said second position comprises a spring element having one end secured to said cover and having another end immobilized with respect to said cup member.

5. The collector of claim 4 in which said deflecting portion of said cover means is generally circular in configuration and said spring element is secured to said deflecting portion along one edge thereof; said water-soluble portion of said cover means being secured to said deflecting portion and said cup member at a point along the edge of said deflecting portion opposite from said spring element.

6. The collector of claim 3 in which said means for urging said deflecting portion of said cover means into its second position comprises the mouth of said cup member extending along an inclined plane, said deflecting portion being slidable away from the mouth of said cup member under the influence of gravity when said water-soluble portion of said cover means is dissolved.

7. The collector of claims 1 or 2 in which said water-soluble portion of said cover means extends over the mouth of said cup member and deflects urine flowing into said passage through said inlet when said cover means is in said first operative state; said water-soluble portion being dissolved to expose the mouth of said cup member when said cover means is in said second operative state.

8. The collector of claim 7 in which said water-soluble portion of said cover is generally dome-shaped.

9. The collector of claim 8 in which support means extends over the mouth of said cup member beneath said water-soluble portion of said cover means for supporting the same.

10. The collector of claim 9 in which said support means comprises a framework of struts for supporting said water-soluble portion of said cover means.

11. The collector of claims 1 or 2 in which said water-soluble portion is formed of polyvinyl alcohol.

12. The collector of claim 1 in which said body is funnel-shaped with said inlet being larger than said outlet.

13. The collector of claim 12 in which said funnel-shaped body has a generally frusto-conical upper section and a reduced lower section.

14. The collector of claim 13 in which said cup member is disposed in the upper portion of said lower section of said body.

15. The collector of claim 14 in which said frustoconical upper section includes an annular flange extension projecting downwardly and inwardly into the upper portion of said lower section above said cup member; said flange extension being provided with a plurality of circumferentially-spaced recesses having the outer limits thereof aligned with said flow passage radially outwardly of said cup member.

16. The collector of claims 12, 13, or 14 in which said cup member is coaxial with said body.

17. A sterile midstream urine collector comprising a tubular body having an upper inlet, a lower outlet, and a flow passage therebetween; a cup member having an upwardly-directed mouth and being mounted within said passage below said inlet; said cup member being substantially smaller than said passage to permit the downward flow of urine through said passage past said cup member; and urine-deflecting cover means having at least a portion thereof formed of a non-contaminating water-soluble polymeric material capable of disintegrating within 2 to 15 seconds upon direct exposure to a stream of urine; said cover means having a first operative state in which said water-soluble portion is intact and said cover means closes the mouth of said cup member and deflects the initial portion of a stream of urine entering said passage and impinging on said cover, and a second operative state wherein said water-soluble portion is dissolved by exposure to an initial portion of a stream of urine and the mouth of said cup member is exposed to receive an uncontaminated subsequent portion of said stream; and means defining an evacuation passage communicating with said cup member.

18. The collector of claim 17 in which said water-soluble polymeric material is capable of disintegrating within 3 to 8 seconds upon direct exposure to a stream of urine.

19. The collector of claim 17 in which said cover means includes a water-insoluble deflecting portion normally disposed in a first position extending over the mouth of said cup member when said cover means is in said first operative state, and means urging said deflecting portion into a second position displaced from the mouth of said cup member when said cover means is in its second operative state; said water-soluble portion of said cover means normally holding said deflecting portion in its first position but allowing said deflecting portion to shift into said second position when said water-soluble portion is dissolved.

20. The collector of claim 19 in which said means for urging said deflecting portion into said second position comprises a spring element having one end secured to said cover and having another end immobilized with respect to said cup member.

21. The collector of claim 20 in which said deflecting portion of said cover means is generally circular in configuration and said spring element is secured to said deflecting portion along one end thereof; said water-soluble portion of said cover means being secured to said deflecting portion and said cup member a point along the edge of said deflecting portion opposite from said spring element.

22. The collector of claim 19 in which said means for urging said deflecting portion of said cover means into its second position comprises the mouth of said cup member extending along an inclined plane, said deflecting portion being slidable away from the mouth of said cup member under the influence of gravity when said water-soluble portion of said cover means is dissolved.

23. The collector of claim 17 in which said water-soluble portion of said cover means extends over the mouth of said cup member and deflects urine flowing into said passage through said inlet when said cover means is in its first operative state; said water-soluble portion being dissolved to expose the mouth of said cup member when said cover means is in its second operative state.

24. The collector of claim 23 in which said water-soluble portion of said cover is generally dome-shaped.

25. The collector of claims 17, 19, 20, 22, or 23 in which said means defining said evacuation passage communicates with said cup member at the lower end thereof; and means provided by said body for supporting a container communicable with said evacuation passage means for receiving urine collected by said cup member.

26. The collector of claim 25 in which said means defining said evacuation passage includes a tubular spike having a pointed end adapted to penetrate the membrane of the stopper of a collection tube.

27. The collector of claim 26 in which said means for removably supporting a container communicable with said evacuation passage means comprises a guideway for slidably supporting a collection tube adjacent said spike.

28. The collector of claim 27 in which a collection tube is slidably supported within said guideway and has a membrane oriented for engagement with said spike for the piercing of said membrane and the withdrawal of urine from said cup member into said collection tube when the membrane of said collection tube is pierced by said spike.

29. The collector of claim 26 in which a collection tube in the form of a syringe is removably supported by said supporting means; said syringe having a tip equipped with a resilient self-sealing stopper into which said spike projects.

30. The collector of claim 29 in which said supporting means comprises a housing defining an open-topped cavity for removably supporting said syringe; said syringe being supported for limited tipping movement within said cavity; and a resilient member within said cavity engaging said syringe and restraining tipping movement thereof.

31. The collector of claim 17 in which said body is funnel-shaped with said inlet being larger than said outlet.

32. The collector of claim 31 in which said funnel-shaped body has a generally frusto-conical upper section and a reduced lower section.

33. The collector of claim 32 in which said cup member is disposed in the upper portion of said lower section of said body.

34. The collector of claim 33 in which said cup member is coaxial with said body.

35. The collector of claim 17 in which said water-soluble portion of said cover means is formed of polyvinyl alcohol.

36. A sterile midstream urine collector comprising a tubular body having an upper inlet, a lower outlet, and a flow passage therebetween; a cup member having an upwardly-directed mouth and being mounted within said passage below said inlet; said cup member being substantially smaller than said passage to permit the downward flow of urine through said passage past said cup member; urine-deflecting cover means having at least a portion thereof formed of a non-contaminating water-soluble polymeric material capable of disintegrating within about 2 to 15 seconds upon direct exposure to a stream of urine; said cover means having a first operative state wherein said water-soluble portion is intact and said cover means closes the mouth of said cup member and deflects the initial portion of a stream of urine entering said passage and impinging on said cover, and a second operative state wherein said water-soluble portion of said cover means is dissolved by exposure to an initial part of a stream of urine and the mouth of said cup member is exposed to receive an uncontaminated subsequent part of said stream; means defining an evacuation passage communicating with said cup member and including a tubular spike adapted to extend through and be removable from a self-sealing stopper of a sample collection tube; and means provided by said collector for removably supporting a collection tube adjacent said body.

37. The collector of claim 36 in which said means defining said evacuation passage communicates with said cup member at the lower end thereof.

38. The collector of claim 36 in which said means for supporting a collection tube includes a guideway; and an air-evacuated collection tube is slidably supported by said guideway and has a membrane oriented for engagement with said spike for the piercing of said membrane and the withdrawal of urine from said cup member into said collection tube when the membrane of said collection tube is pierced by said spike.

39. The collector of claim 36 in which said cover means includes a water-insoluble deflecting portion normally disposed in a first position extending over the mouth of said cup member when said cover means is in said first operative state, and means urging said deflecting portion into a second position displaced from the mouth of said cup member when said cover means is in its second operative state; said water-soluble portion of said cover means normally holding said deflecting portion in its first position but allowing said deflecting portion to shift into said second position when said water-soluble portion is dissolved.

40. The collector of claim 39 in which said means urging said deflecting portion into said second position comprises a spring element having one end secured to said cover and another end immobilized with respect to said cup member.

41. The collector of claim 40 in which said deflecting portion of said cover is generally circular in configuration and said spring element is secured to said deflecting portion along one edge thereof; said water-soluble portion of said cover means being secured to said deflecting portion and said cup member at a point along the edge of said deflecting portion opposite from said spring element.

42. The collector of claim 39 in which said means for urging said deflecting portion of said cover means into its second position comprises the mouth of said cup member extending along an inclined plane, said deflecting portion being slidable away from the mouth of said cup member under the influence of gravity when said water-soluble portion of said cover means is dissolved.

43. The collector of claim 39 in which said water-soluble portion is formed of polyvinyl alcohol.

44. The collector of claim 36 in which said water-soluble portion of said cover means extends over the mouth of said cup member and deflects urine flowing into said passage through said inlet when said cover means is in its first operative state; said water-soluble portion being dissolved to expose the mouth of said cup member when said cover means is in its second operative state.

45. The collector of claim 44 in which said water-soluble portion of said cover is generally dome-shaped.

46. The collector of claim 45 in which support means extends over the mouth of said cup member beneath said water-soluble portion of said cover means for supporting the same.

47. The collector of claim 46 in which said support means comprises a framework of struts for supporting said water-soluble portion of said cover means.

48. The collector of claim 36 in which a collection tube in the form of a syringe is removably supported adjacent said body; said syringe having a tip equipped with a stopper into which said spike projects.

49. The collector of claim 48 in which said tubular spike is flexible.

50. The collector of claim 49 in which said collector includes a housing defining an open-topped cavity for removably supporting said syringe adjacent said body; said syringe being supported for limited tipping movement within said cavity; and a resilient member within said cavity engaging said syringe and restraining tipping movement thereof.

* * * * *